(12) United States Patent
Hufford et al.

(10) Patent No.: US 12,144,573 B2
(45) Date of Patent: *Nov. 19, 2024

(54) DYNAMIC CONTROL OF SURGICAL INSTRUMENTS IN A SURGICAL ROBOTIC SYSTEM

(71) Applicant: Asensus Surgical US, Inc., Durham, NC (US)

(72) Inventors: Kevin Andrew Hufford, Durham, NC (US); Matthew Robert Penny, Durham, NC (US); Mohan Nathan, Durham, NC (US); Glenn Warren, Durham, NC (US)

(73) Assignee: Asensus Surgical US, Inc., Durham, NC (US)

( * ) Notice: Subject to any disclaimer, the term of this patent is extended or adjusted under 35 U.S.C. 154(b) by 507 days.

This patent is subject to a terminal disclaimer.

(21) Appl. No.: 17/564,090

(22) Filed: Dec. 28, 2021

(65) Prior Publication Data

US 2022/0117686 A1 Apr. 21, 2022

Related U.S. Application Data

(63) Continuation of application No. 16/236,636, filed on Dec. 30, 2018, now Pat. No. 11,234,781.

(Continued)

(51) Int. Cl.
*A61B 34/37* (2016.01)
*A61B 34/00* (2016.01)
(Continued)

(52) U.S. Cl.
CPC .............. *A61B 34/37* (2016.02); *A61B 34/20* (2016.02); *A61B 34/25* (2016.02); *A61B 34/30* (2016.02);
(Continued)

(58) Field of Classification Search
CPC ......... A61B 34/37; A61B 34/20; A61B 34/25; A61B 34/30; A61B 34/70; A61B 34/74;
(Continued)

(56) References Cited

U.S. PATENT DOCUMENTS 8,620,473 B2  12/2013  Diolaiti et al.
10,271,912 B2  4/2019  Diolaiti et al.
(Continued)

OTHER PUBLICATIONS

Power et al., "A cooperative control framework for haptic guidance of bimanual surgical tasks based on Learning From Demonstration," 2015 IEEE International Conference on Robotics and Automation (ICRA), Seattle, WA, USA, 2015, pp. 5330-5337, doi: 10.1109/ICRA.2015.7139943. (Year: 2015).*

(Continued)

*Primary Examiner* — Carlos A Rivera
*Assistant Examiner* — Cherie M Poland

(57) ABSTRACT

A robotic surgical system configured to control movement of a first instrument and a second instrument, each of which is on a robotic manipulator. In described modes of operation, movement of the first instrument is surgeon controlled based on surgeon input to the robotic system. Movement of the second instrument is also surgeon controlled, but its motion is defined by the chosen mode of operation which sets the amplitude and direction of the second instrument's motion relative to the actual or instructed motion of the first instrument. In this way, two instruments are simultaneously moved based on input from a single surgeon input device.

14 Claims, 2 Drawing Sheets

Related U.S. Application Data

(60) Provisional application No. 62/612,548, filed on Dec. 31, 2017.

(51) Int. Cl.
    *A61B 34/20*     (2016.01)
    *A61B 34/30*     (2016.01)
    *A61B 90/00*     (2016.01)
    *A61B 17/00*     (2006.01)

(52) U.S. Cl.
    CPC .............. *A61B 34/70* (2016.02); *A61B 34/74* (2016.02); *A61B 90/361* (2016.02); *A61B 2017/00216* (2013.01); *A61B 2017/00973* (2013.01); *A61B 2034/743* (2016.02)

(58) Field of Classification Search
    CPC ............ A61B 90/361; A61B 2037/743; A61B 2017/00216; A61B 2017/00973
    See application file for complete search history.

(56) References Cited

U.S. PATENT DOCUMENTS

| | | | |
|---|---|---|---|
| 10,299,883 | B2 | 5/2019 | Kilroy |
| 2007/0282228 | A1 | 12/2007 | Einav et al. |
| 2011/0276058 | A1 | 11/2011 | Choi et al. |
| 2013/0198625 | A1 | 8/2013 | Anderson et al. |
| 2015/0038982 | A1* | 2/2015 | Kilroy ................. A61B 90/361 606/130 |
| 2015/0297177 | A1 | 10/2015 | Boctor et al. |
| 2016/0184032 | A1 | 6/2016 | Romo et al. |
| 2016/0270867 | A1 | 9/2016 | Scholan |
| 2017/0086932 | A1 | 3/2017 | Auld et al. |
| 2017/0189126 | A1 | 7/2017 | Weir |
| 2017/0189130 | A1 | 7/2017 | Weir |
| 2017/0189131 | A1 | 7/2017 | Weir |
| 2017/0360522 | A1 | 12/2017 | Beira |
| 2018/0185110 | A1 | 7/2018 | Kumar et al. |
| 2018/0311005 | A1 | 11/2018 | Mccormick et al. |
| 2019/0125462 | A1 | 5/2019 | Peine et al. |
| 2019/0201107 | A1 | 7/2019 | Hufford |
| 2019/0202066 | A1 | 7/2019 | Maret |
| 2020/0367978 | A1 | 11/2020 | Gonenc et al. |
| 2020/0397520 | A1 | 12/2020 | Penny et al. |

OTHER PUBLICATIONS

Hagn et al., "DLR MiroSurge: a versitile system for research in endoscopic telesurgery." Int J Cars. DOI 10.007/s11548-009-0372-4. ePub Jun. 13, 2009. 11 pages (Year: 2009).*

* cited by examiner

DYNAMIC CONTROL OF SURGICAL INSTRUMENTS IN A SURGICAL ROBOTIC SYSTEM

This application is a continuation of U.S. application Ser. No. 16/236,636, filed Dec. 30, 2018, which claims the benefit of U.S. Provisional Application No. 62/612,548, filed Dec. 31, 2017.

BACKGROUND

There are various types of surgical robotic systems on the market or under development. Some surgical robotic systems use a plurality of robotic arms. Each arm carries a surgical instrument, or the camera used to capture images from within the body for display on a monitor. See U.S. Pat. No. 9,358,682, which is incorporated herein by reference. Other surgical robotic systems use a single arm that carries a plurality of instruments and a camera that extend into the body via a single incision. See WO 2016/057989, which is incorporated herein by reference. Each of these types of robotic systems uses motors to position and/or orient the camera and instruments and to, where applicable, actuate the instruments. Typical configurations allow two or three instruments and the camera to be supported and manipulated by the system. Input to the system is generated based on input from a surgeon positioned at a master console, typically using input devices such as input handles and a foot pedal. Motion and actuation of the surgical instruments and the camera is controlled based on the user input. The image captured by the camera is shown on a display at the surgeon console. The console may be located patient-side, within the sterile field, or outside of the sterile field.

US Patent Publication US 2010/0094312 (the '312 application), incorporated herein by reference, describes a surgical robotic system in which sensors are used to determine the forces that are being applied to the patient by the robotic surgical tools during use. This application describes the use of a 6 DOF force/torque sensor attached to a surgical robotic manipulator as a method for determining the haptic information needed to provide force feedback to the surgeon at the user interface. It describes a method of force estimation and a minimally invasive medical system, in particular a laparoscopic system, adapted to perform this method. As described, a robotic manipulator has an effector unit equipped with a six degrees-of-freedom (6-DOF or 6-axes) force/torque sensor. The effector unit is configured for holding a minimally invasive instrument mounted thereto. In normal use, a first end of the instrument is mounted to the effector unit of the robotic arm and the opposite, second end of the instrument (e.g. the instrument tip) is located beyond an external fulcrum (pivot point kinematic constraint) that limits the instrument in motion. In general, the fulcrum is located within an access port (e.g. the trocar) installed at an incision in the body of a patient, e.g. in the abdominal wall. A position of the instrument relative to the fulcrum is determined. This step includes continuously updating the insertion depth of the instrument or the distance between the (reference frame of the) sensor and the fulcrum. Using the 6 DOF force/torque sensor, a force and a torque exerted onto the effector unit by the first end of the instrument are measured. Using the principle of superposition, an estimate of a force exerted onto the second end of the instrument based on the determined position is calculated. The forces are communicated to the surgeon in the form of tactile haptic feedback at the hand controllers of the surgeon console.

In a laparoscopic surgical procedure performed using manual instruments, the surgeon manipulates the primary instruments while a surgical assistant controls the camera and third instrument. Giving the surgeon control over the camera and the third instrument is an important improvement over traditional laparoscopy, these two implements are no longer controlled dynamically as they are when manually handled by a user.

U.S. Pat. No. 9,360,934 describes a robotic system allowing dynamic surgeon control of the robotic manipulator that supports the camera by allowing the surgeon to control the camera using an eye tracking system. The other two or three robotic manipulators carrying surgical instruments are driven via handles in a surgeon console. Since the surgeon has just two hands, operation of the system in procedures utilizing more than two surgical instruments on robotic manipulators requires the surgeon to choose which two instruments s/he will control using the console at any given moment. This application describes certain modes of operation that enable dynamic, surgeon-controlled movement of a third instrument while also controlling the two primary instruments.

Although the inventions described herein may be used on a variety of robotic surgical systems, the embodiments will be described with reference to the system shown in FIG. 1. In the illustrated system, a surgeon console 12 has two input devices such as handles 17, 18 that the surgeon selectively assigns to robotic arms 14, 15, 16, allowing surgeon control of two of the surgical instruments 10a, 10b, and 10c disposed at the working site at any given time. To control a third instrument disposed at the working site, one of the two handles 17, 18 is operatively disengaged from one of the initial two instruments and then operatively paired with the third instrument. (Note that in FIG. 1 the laparoscopic camera, which may be a robotically positioned camera supported by a fourth robotic arm, is not shown for purposes of clarity.)

A control unit 30 is operationally connected to the robotic arms and to the user interface. The control unit receives user input from the input devices corresponding to the desired movement of the surgical instruments, and the robotic arms 14, 15 and 16 are caused to manipulate the surgical instruments accordingly.

DETAILED DESCRIPTION

Figure 1:
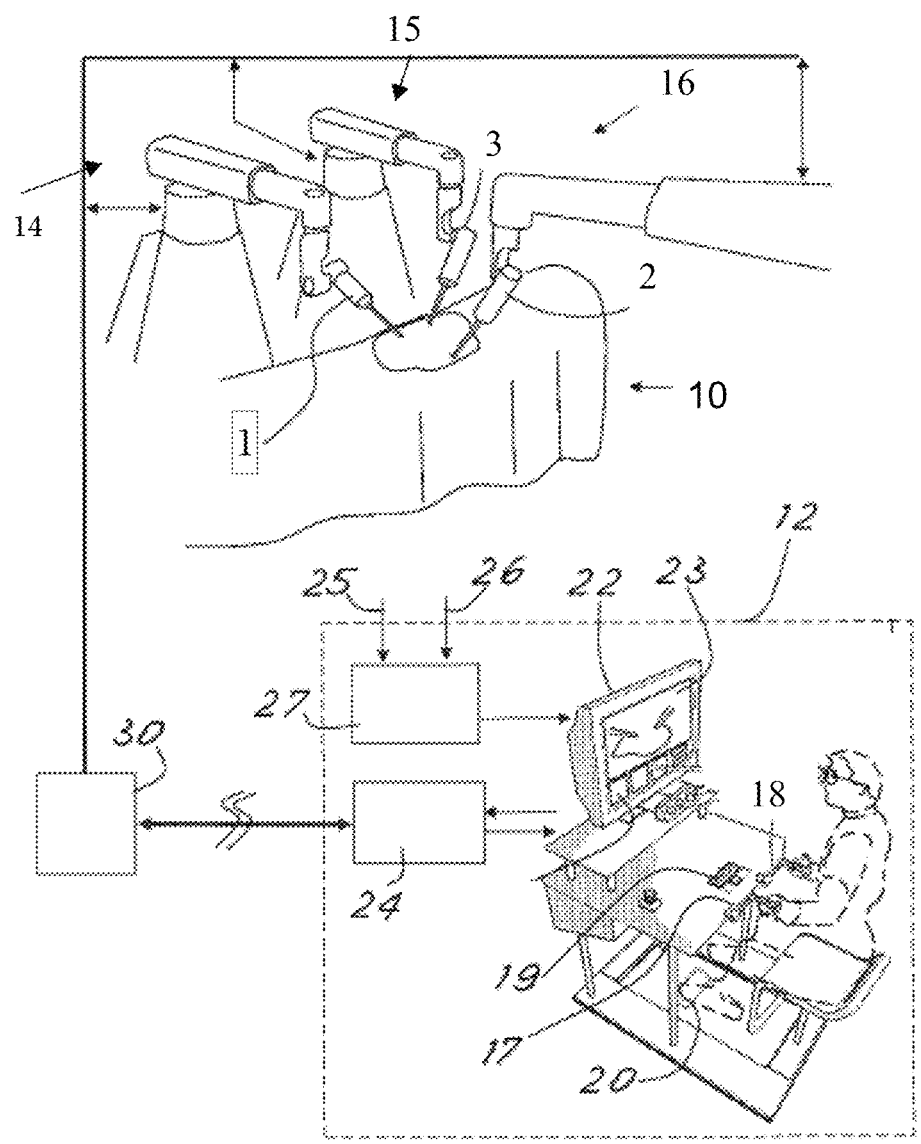
FIG. 1 schematically illustrates elements of a surgical robotic system of a type that may be adapted for use with the disclosed invention.

The present application describes a system and method for maintaining optimal tissue tension between instruments of a surgical robotic system.

The surgical system may be of a type described in the Background, or any other type of robotic system used to maneuver surgical instruments at an operative site within the body. In some embodiments, the surgical system is one that includes sensors positioned to estimate the forces each robotically manipulated surgical instrument applies to tissue. Configurations such as those described in US Patent Publication US 2010/0094312, or other configurations, can be used for this purpose.

In this description, the terms "primary instruments" will refer to the surgical instruments moveable by robotic manipulators based directly on input delivered to the system by the surgeon inputs at the surgeon console. The term "secondary instrument" or "third instrument" will refer to a third instrument that is also moveable by a robotic manipulator, but whose movement characteristics (e.g. direction, orientation) is based in some way on the characteristics of the directed movement of the one of the primary instruments that is operating under the control input from the surgeon console. While it will be typical for two primary instruments to be used, in some embodiments there might just be one primary instrument. For example, there might just be one primary instrument in a configuration where only one instrument is being controlled by a user input handle because the other user input handle is controlling the camera rather than using eye tracking or some other form of input.

This application describes two modes that may be implemented to control movement of a secondary instrument. These are referred to as the modes of Mirrored Motion and Matched Motion. When entering one of these modes of operation, control of the secondary instrument is such that the secondary instrument either follows the movement of one of the primary instruments, or mirrors the movement of one of the primary instruments.

The surgeon console includes a user interface that allows the user to select a mode of operation. The user interface used to select the mode may include any type of input device, such as a button or other input on the input handles, a graphical user interface, voice input, eye tracking input, foot pedal, keyboard, touch sensitive surface, etc. Because these modes of motion may only be desired for specific tasks, it is preferred that the user interface allow these modes to be easily activated, and de-activated, when desired. The user interface may also allow the user to select the instrument that is to function as the primary instrument and the instrument that is to function as the secondary instrument.

For example, using the example of buttons on each of the surgeon input handles, if the button held is on the left handle of the user interface, the left instrument would be the primary instrument and the secondary instrument would either follow in matched or mirrored motion. Whereas if the button is held on the right handle, the right instrument would be the primary.

Turning first to mirror motion, this is a mode in which motion of the secondary instrument mirrors the motion of a primary instrument. The determination of the direction of motion of the secondary instrument might be determined based on the surgeon input at the console handle for the primary instrument, or it might be determined in another way (e.g. by directly monitoring the position of the primary instrument using computer vision or by calculating its position using sensors associated with the robotic manipulator supporting it).

Figure 2:
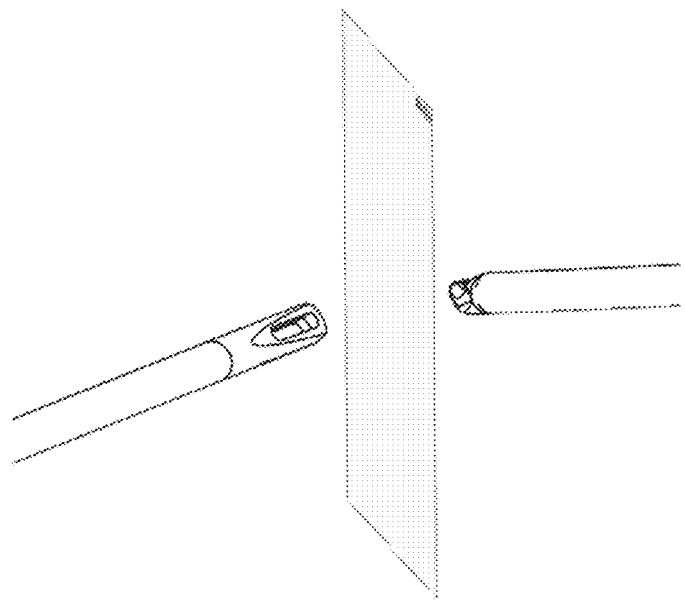
FIGS. 2 and 3 schematically illustrate the use of robotically-controlled traction and surgeon-controlled traction according to an aspect of the disclosed invention.

Use of mirror mode involves first defining the plane between the primary instrument and the secondary instrument about which the motion is mirrored. FIG. 2 illustrates a primary instrument and a secondary instrument separated by a plane. When the mirrored mode of operation is engaged, the tip of the secondary instrument will follow the first instrument tip as if mirrored by the plane. If the first instrument moves up, down, left, or right, relative to the mirror, the second instrument will follow in amplitude and direction. However, if the first instrument moves towards the mirror plane, the second instrument will also approach the mirror plane. Likewise, if the first instrument moves away from the plane, the second instrument will move away from the plane as well.

It should be noted, that, unlike a typical mirror, the starting position of the instrument tips relative to the mirror plane may not be identical. As an example, the first instrument may intersect the mirror plane at a different location than the second instrument when they both approach the mirror plane. Typically, though, the amplitude of the movement of the primary and secondary instruments, from their respective origins, is the same and the direction of the motion, relative to the mirror plane is maintained.

The control of the jaw opening and closing may be optionally included in mirrored motion operation. In some embodiments, the surgeon may selectively turn on/off mirrored jaw motion when within the mirror mode.

The plane about which motion is mirrored could have a default position and orientation programmed into the system. For example, the plane could bisect the angle between the instruments, or the plane could be perpendicular to the camera view. Alternatively, the user may be able to select the desired plane using the user interface, and optionally to adjust the plane during use of mirror mode. Alternatively, the orientation may be selected or adjusted by the system. For example, a system equipped with capabilities to assess tissue planes (for example using structured light techniques) and/or cavity volumes (time of flight, 3D, etc.) may be able to adjust the orientation of the mirror plane to optimize the movement of both the primary and secondary instruments while avoiding inadvertent contact between either and adjacent tissue. For example, in tight working spaces, where there is less room for lateral, side-to-side, instrument motion, the mirror plane may be adjusted such that the instruments are either pulled or pushed along an insertion axis of the instrument.

Figure 3:
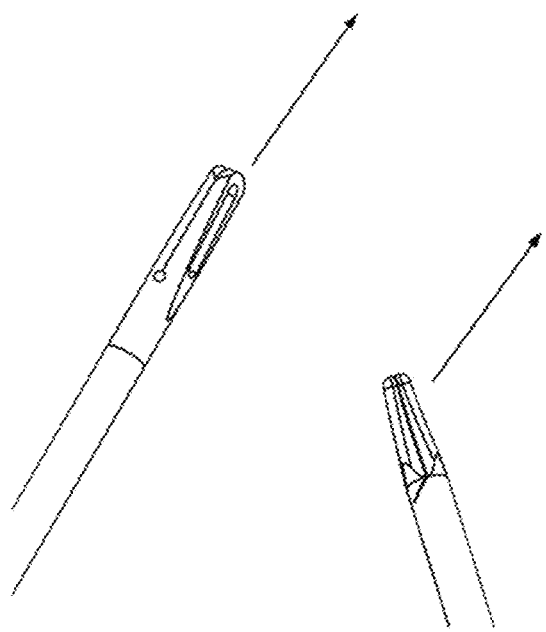

In the "matched" mode of operation, the first and second instruments move in tandem, based on the amplitude and direction of the motion of the first instrument. See FIG. 3. This mode differs from mirrored mode primarily in that matched motion does not have any degree of freedom that is reflected, as in a mirror. The amplitude and direction of the first instrument is replicated by the second instrument, from its point of origin. In a variation of this embodiment, a user-selected or system-selected scaling factor may be applied, so that the amplitude of movement of the secondary instrument is lower or higher than that of the primary instrument by some scaling factor. In another variation, the movement of the instruments may be matched in amplitude, but the direction may be differ. In this embodiment, the direction of movement may be defined by the vector of the instrument shaft (e.g. along the longitudinal axis of the shaft). The vector for each instrument may be determined using the kinematics of the robotic manipulator, and/or based on the interoperative view captured by the laparoscope (using, for example, a computer vision algorithm to detect the instrument and its orientation). Matched mode may be used for a variety of applications, including one that allows the secondary instrument to be kept in proximity to the primary instrument. This allows the secondary instrument to remain in the surgeon's field of view on the visual display, so the surgeon can readily exit matched mode and then assign the instrument that had been serving as a secondary instrument to a handle of the console, allowing direct control of that instrument with the handle.

The described modes allow for dynamic control over a third instrument in a robotic surgical system where first and second instruments are controlled using surgeon inputs, thus letting the surgeon operate three instruments with two hands in specific scenarios by configuring the system so that two surgical instruments (a primary and a secondary) may be driven based on the movement of a single master input device.

All patents and applications referred to herein, including for purposes of priority, are incorporated herein by reference.

We claim:

1. A surgical method, comprising:
   providing a surgical robotic system having a first robotic manipulator with a first surgical instrument thereon, a second robotic manipulator with a second surgical instrument thereon, and first and second user input devices;
   receiving user input from the first input device and the second input device;
   in a first mode of operation, simultaneously moving each of the first and second surgical instruments in response to user input from only the first user input device, wherein said moving step includes moving the first surgical instrument with a first amplitude and first direction and moving the second surgical instrument with a second amplitude and second direction, wherein the second amplitude differs from the first amplitude;
   in a second mode of operation, moving the first surgical instrument in response to user input from the first user input device, and moving the second surgical instrument in response to user input from the second user input device.

2. The method of claim 1, wherein the second direction equals the first direction.

3. The method of claim 1, wherein the second direction differs from the first direction.

4. The method of claim 3, wherein the first direction is oriented along a first longitudinal axis of the first surgical instrument, and wherein the second direction is oriented along a second longitudinal axis of the second surgical instrument.

5. The method of claim 1, further including the step of receiving user input instructing the system to operate in the first mode or the second mode.

6. The method of claim 1, wherein simultaneously moving each of the first and second surgical instruments in response to user input from only the first user input device includes generating instructions to control movement of the first and second surgical instruments based on movement of the first user input device.

7. The method of claim 1, wherein simultaneously moving each of the first and second surgical instruments in response to user input from only the first user input device includes:
   generating instructions to control movement of the first surgical instrument based on movement of the first user input device;
   capturing images of the first surgical instrument;
   applying computer vision to the images to determine the first direction and the first amplitude; and
   generating instructions to control movement of the second surgical instrument based on the determined first direction and first amplitude.

8. The method of claim 1, wherein simultaneously moving each of the first and second surgical instruments in response to user input from only the first user input device includes:
   generating instructions to control movement of the first surgical instrument based on movement of the first user input device;
   receiving kinematic data from the first manipulator and determining the first direction and the first amplitude from the kinematic data; and
   generating instructions to control movement of the second surgical instrument based on the determined first direction and first amplitude.

9. A surgical method, comprising:
   providing a surgical robotic system having a first robotic manipulator with a first surgical instrument thereon, a second robotic manipulator with a second surgical instrument thereon, and first and second user input devices;
   receiving user input from the first input device and the second input device;
   in a first mode of operation, simultaneously moving each of the first and second surgical instruments in response to user input from only the first user input device, wherein said moving step includes moving the first surgical instrument with a first amplitude and first direction and moving the second surgical instrument with a second amplitude and second direction;
   in a second mode of operation, moving the first surgical instrument in response to user input from the first user input device, and moving the second surgical instrument in response to user input from the second user input device;
   wherein simultaneously moving each of the first and second surgical instruments in response to user input from only the first user input device includes:
   generating instructions to control movement of the first surgical instrument based on movement of the first user input device;
   capturing images of the first surgical instrument;
   applying computer vision to the images to determine the first direction and the first amplitude; and
   generating instructions to control movement of the second surgical instrument based on the determined first direction and first amplitude.

10. The method of claim 9, wherein the second direction equals the first direction.

11. The method of claim 9, wherein the second direction differs from the first direction.

12. The method of claim 11, wherein the first direction is oriented along a first longitudinal axis of the first surgical instrument, and wherein the second direction is oriented along a second longitudinal axis of the second surgical instrument.

13. The method of claim 9, wherein the second amplitude differs from the first amplitude.

14. The method of claim 9, further including the step of receiving user input instructing the system to operate in the first mode or the second mode.

* * * * *